United States Patent [19]
Goodman et al.

[11] Patent Number: 6,028,098
[45] Date of Patent: Feb. 22, 2000

[54] USE OF CIS-OR TRANSUROCAMIC ACID FOR THE TREATMENT OF PHOTODERMATOSES AND IMMUNOGENIC SKIN DISEASES

[75] Inventors: Michael Goodman, Ampthill; James Ferguson, Fife, both of United Kingdom

[73] Assignee: Bioglan Ireland (R&D) Limited, Dublin, Ireland

[21] Appl. No.: 08/530,096

[22] PCT Filed: Mar. 29, 1994

[86] PCT No.: PCT/GB94/00650

§ 371 Date: Feb. 9, 1996

§ 102(e) Date: Feb. 9, 1996

[87] PCT Pub. No.: WO94/22441

PCT Pub. Date: Oct. 13, 1994

[30] Foreign Application Priority Data

Mar. 29, 1993 [GB] United Kingdom ............ 9306473

[51] Int. Cl.⁷ .................................................. A61K 31/40
[52] U.S. Cl. ................... 514/427; 514/861; 514/863; 514/885; 514/887; 548/561; 548/562
[58] Field of Search ........................ 548/561, 562; 514/427, 861, 863, 885, 887

[56] References Cited

U.S. PATENT DOCUMENTS

| | | | |
|---|---|---|---|
| 5,147,872 | 9/1992 | Golwyn | 514/219 |
| 5,455,036 | 10/1995 | Stab et al. | 424/401 |
| 5,494,676 | 2/1996 | Stab et al. | 424/401 |
| 5,501,849 | 3/1996 | Lee | 424/59 |
| 5,620,680 | 4/1997 | Stab et al. | 424/59 |
| 5,723,482 | 3/1998 | Degwert et al. | 514/399 |

FOREIGN PATENT DOCUMENTS

| | | |
|---|---|---|
| 467116 | 1/1992 | European Pat. Off. . |
| 1003922 | 3/1957 | Germany . |
| 1235506 | 3/1967 | Germany . |
| 4122497 | 7/1991 | Germany . |
| 4122497 | 1/1993 | Germany . |
| B1 22 16 33 | 3/1990 | New Zealand . |
| 92/17208 | 10/1992 | WIPO . |

OTHER PUBLICATIONS

Concar, New Scientist, May 16, 1992, 23–28.
Diezel, Chemical Abstracts, 118:116750 (1993).
Medline Abstract No. 78249136, 1978 Davies et al., "Dermatitis Herpetiformis— a skin manifestation of a generalized disturbance in immunity", Quarterly J. of Med., Apr. 1978, 47 (186) 221–48.
Medline Abstract No. 91101139, 1991, Walsh et al., "Immunopathognesis of Oral Lichen Planus", J. of Oral Pathology and Medicine, Oct. 1990, 19(9) 389–96.
Baadsgaard et al., "The Role of the Immune System in the Pathogenesis of Psoriasis", J. Invest. Dermatol., 95(5) 32S–34S, 1990.
Ferguson et al., "Elevated IgG Immune Complexes in Children with Atopic Eczema", J. Allergy Clin. Immunol., 74(5) 678–682, 1984.
Gottlieb, "Immunologic Mechanisms in Psoriasis", J. Invest. Dermatol., 95(5), 18S–19S, 1990.
English translation of German Patent No. 4122497.
Norval et al., Photochem. Photobiol., 49(5), 633–639, 1989.
Wille et al., Chemical Abstracts, 121:246306 (1994).

*Primary Examiner*—Fiona T. Powers
*Attorney, Agent, or Firm*—Wolf, Greenfield & Sacks, P.C.

[57] ABSTRACT

A compound of the general formula (I): Q—R—X wherein Q is a substituted or unsubstituted furanyl, imidazolyl, pyrrolyl or thiopheneyl group, R is $CR^1_2$—$Cr^2_2$, (cis) $CR^1=CR^2$, or (trans)-$CR^1=CR^2$, X is $COOR^3$ or $NR^1R^4$, and $R^1$–$R^4$ are each, independently, H, an alkyl or an aryl group and pharmaceutically acceptable salts thereof, are described for use in topical treatments of skin conditions which involve an overactive immune response, or which are responsive to UV irradiation. Pharmaceutical compositions of the compound of general formula (I) are also described.

14 Claims, No Drawings

USE OF CIS-OR TRANSUROCAMIC ACID FOR THE TREATMENT OF PHOTODERMATOSES AND IMMUNOGENIC SKIN DISEASES

DESCRIPTION

The present invention relates to compounds of general formula I:

Q—R—X     (I)

wherein Q is a substituted or unsubstituted furanyl, imidazolyl, pyrrolyl or thiopheneyl group, R is $CR^1_2$—$CR^2_2$, (cis)$CR^1$=$CR^2$, or (trans)$CR^1$=$CR^2$, X is $COOR^3$ or $NR^1R^4$, and $R^1$–$R^4$ are each, independently, H, or an alkyl or an aryl group and to pharmaceutically acceptable salts thereof. The invention also relates to the use of such compounds in the topical treatment of skin conditions considered to involve an over-active immune response, or which are responsive to ultraviolet (UV) radiation.

Trans-urocanic acid (UCA) is a naturally occurring compound found in the upper layers of the epidermis, where it is synthesized through deamination of histidine by histidase. When the skin is irradiated with ultraviolet light, up to 60 or 70% of the trans-UCA present is converted into the cis-isomer and it is thought that cis-UCA, once so generated, functions as a mediator in both systemic and local UV induced immune system suppression. See the review article by M. Norval et al. in Photochemistry and Photobiology Vol. 50. No. 2, pp 267–275, 1989 (1).

Support for the proposition that cis-UCA is a mediator in UV induced suppression of the immune system is provided by the work reported by M. Norval et al. in Photochemistry and Photobiology Vol. 49. No. 5, pp 633–639, 1989 and that of V. E. Reeve et al., reported in Photodermatol Photoimmunol Photoreed 1991: 8: pp 176–180. The former authors found that cis-UCA was able to induce suppression of normal delayed type hypersensitivity response to herepes simplex virus type 1 in mice and the latter found that cis-UCA, generated by applying trans-UCA (in a cosmetic cream) to murine skin and then irradiating the treated skin, systemically suppressed normal contact hyper-sensitivity. Reeve et al. suggested that this activity is potentially harmful, since it could result in tumour development and, therefore, concluded that urocanic acid was potentially hazardous and should not be used as a cosmetic ingredient. Indeed, Reeve et al., in Photochemistry and Photobiology Vol. 49. No. 4. pp 459–464. 1989., reported that topically applied trans-UCA significantly increased the tumour load induced in hairless mice, on exposure to Erythema inducing doses of UV light or sunlight.

Thus, rather than being confirmed as therapeutically useful, investigation of their metabolic roles has led to the removal of trans-UCA from various commercially available cosmetic creams (see Concar in the New Scientist, May 16, 1992), to obviate the risk of it being transformed into the apparently harmful cis-isomer, and to cis-UCA being considered of potential use only in the treatment of serious or life-threatening conditions, such as those involving transplant surgery, etc. For example, cis-UCA has been suggested as a possible immuno-suppressive agent for use in transplant surgery, particularly in skin grafting.

However, contrary to the indications discussed above, it has now been found that certain UCA isomers, derivatives and analogues can be therapeutically useful. Accordingly, the present invention provides a compound of general formula I

Q—R—X     (I)

wherein Q, R and X are as hereinbefore defined, or a pharmaceutically acceptable salt thereof, for use in a topical treatment of a skin condition which involves an over active immune response or which is responsive to UV radiation.

In preferred embodiments of the invention, a compound of general formula (I) can be for use in a method of treating photodermatoses including polymorphic light eruption, photosensitivity, dermatitis/actinic reticuloid syndrome, actinic prurigo and solar urticaria; general urticarias of allergic and non-allergic type; contact sensitivity and skin diseases that respond to UV radiation including, acne vulgaris, alopecia areata, dermatitis herpetiformis, eosinophilic pustular folliculitis, erythrokeratoderma (symmetrical and progressive), chronic lichenoid GVH disease, granuloma annulare, histiocytosis X, ichthyosis linearis circumflexa, lichen planus, pityriasis lichenoides, pityriasis rosea, pityriasis rubra pilaris, pressure sores, pruritis (primary and secondary), seleromyxoedema, subcorneal pustular dermatoses, transient acantholytic dermatoses, psoriasis and atopic eczema. The invention, preferably, can relate to just one or a selection of the aforementioned conditions.

The invention further extends to a method of treating a skin condition considered to involve an over active immune response, or a condition responsive to UV irradiation, inclusive of the specific conditions listed above, or just one or a selection of these conditions.

In a third aspect, the invention provides the use of a compound of general formula (I), as hereinbefore defined, for the manufacture of a medicament for use in the treatment of any one, a selection, or all of the conditions defined, or listed above.

In a further aspect, the present invention provides a pharmaceutical composition, comprising a compound of general formula (I), as hereinbefore defined, in admixture with a pharmaceutically acceptable excipient or carrier and suitable for topical use. Preferably, said composition is for use in treating a condition as hereinbefore defined or listed above.

In embodiments of any aspect of the invention, Q, in general formula (I), can be substituted with F, Cl, Br or —$CH_3$ but, preferably, is unsubstituted; $R^1$–$R^4$ each, independently, can be H, a lower alkyl group (preferably $C_1$–$C_4$) or a phenyl group but, preferably, are H; and R, preferably, is (cis)$CR^1$=$CR^2$.

In all aspects and embodiments of the invention, the preferred compound general formula (I) is cis-UCA. However, the invention encompasses the topical application of trans-UCA and its conversion, in situ, to cis-UCA by irradiation with UV light. The necessary UV light can be provided from an artificial source or by exposure to sunlight. Preferably, the UV is provided using an artificial source.

Preferred pharmaceutical compositions, in accordance with the present invention, comprise ointments, gels, aerosols, wipes, creams, lotions or emulsions which include a compound of general formula I, in admixture with a suitable carrier, mixture of carriers or emulsion thereof.

Cis-UCA can be prepared from the trans-isomer which is available from Sigma UK Ltd. (Poole, Dorset, UK). To prepare the cis-isomer, a solution of trans-UCA at a concentration of 10 mg/ml in dimethyl sulphoxide (or methanol) is spread thinly and irradiated under two Phillips TL20W/L UV lamps for three hours, which provide a total dose of 864 mj/cm2 in the range 270–350 nm. The conversion rate of trans-UCA to cis-UCA is in the order of 70%. Thus, all compositions and preparations, in accordance with the invention, which include cis-UCA can also include trans-UCA and, where quantities of cis-UCA are mentioned, a proportion thereof can be trans-UCA.

Methods of synthesizing other compounds of formula I are set out in M. Norval et al., Photochemistry and Photobiology Vol. 49. No. 5. pp 633–639. 1989.

Pharmaceutical compositions may be prepared by incorporating cis-UCA, prepared in the manner discussed above, into a conventional pharmaceutical cream or other suitable base, using conventional techniques known in the art.

The following examples are provided by way of illustrative embodiments and are not intended in any way to limit the scope of the invention.

EXAMPLE 1

Gel Composition 100 g of a gel composition, suitable for topical application to the skin, were prepared from the following quantities of the following substances;

| | | |
|---|---|---|
| cis-UCA | | 1.0 g |
| Hydroxyethyl cellulose | | 2.0 g |
| Nipasept Sodium | | 0.15 g |
| Glycerol | | 10 g |
| Water | to | 100 g. |

The hydroxyethyl cellulose used was Cellosize QP52, OOOH and was employed as a viscosity enhancer, as well as to provide the composition with the required gel characteristics.

The cis-UCA was prepared from trans-UCA by irradiating a thinly spread solution of 1.0 g of trans-UCA, in dimethyl sulphoxide (10 mg/ml), with two Phillips TL 20 w/l UV lamps for three hours. The conversion rate of trans-UCA to cis-UCA was approximately 70% and, therefore, the cis-UCA used contained up to about 30% trans-UCA. After irradiation, the remaining solvent was removed by evaporation and the cis-UCA was dissolved in a portion of the water. The remaining components were then mixed into the resulting solution and the rest of the water was added to form the final gel.

EXAMPLE 2

Cis-UCA, formed by the irradiation method set out in Example 1, was mixed into a jelly formed from 50% white soft paraffin and 50% liquid paraffin at a concentration of about 2% w/w. The resulting composition was suitable for topical application to the skin.

EXAMPLE 3

Non-aqueous Spray

Non-aqueous sprays in accordance with the invention can be prepared using the following materials in the proportions set out below:

| | | % w/v |
|---|---|---|
| cis-UCA | | 0.1–5 |
| isopropyl isostearate | | 10–40 |
| cyclomethicone | | 10–40 |
| Azone | | 0–20 |
| oil (preferably coconut) | to | 100 |

The preferred composition for such a spray is 2% cis-UCA, 30% isopropyl isostearate, 30% cyclomethicone, 5% azone and 33% coconut oil (all %/w/v).

EXAMPLE 4

Gel Composition

Further gels in accordance with the invention can be prepared using the following materials in the proportions set out below:

| | | % w/w |
|---|---|---|
| cis-UCA | | 0.1–10 |
| Sodium carboxymethy cellulose | | 1.5–2.5 |
| Sorbic acid | | 0.75 |
| Propylene glycol | | 2.0–25 |
| Buffering agent | | 0.01–1 |
| Purified Water | to | 100 |

The preferred composition for such a gel is 5% cis-UCA, 2% sodium carboxymethyl cellulose, 0.75% sorbic acid 10% propylene glycol, 0.1% buffering agent and purified water to 100% (all %w/w).

EXAMPLE 5

Cream Composition

Creams in accordance with the invention can be prepared using the following materials in the proportions set out below:

| | | |
|---|---|---|
| cis-UCA | | 0.1–10 |
| Cosmowax | | 10–25 |
| Oleyl Alcohol | | 0.1–10 |
| Oleic Acid | | 0.1–10 |
| Liquid Paraffin | | 5–25 |
| Polysorbate 20 | | 0.1–5 |
| Phenonip | | 0.1–1 |
| Buffering Agent | | 0.1–1 |
| Sorbic Acid | | 0.075 |
| Purified Water | to | 100 |

The preferred composition for such a cream is 5% cis-UCA, 15% cosmowax, 3% oleyl alcohol, 2% olecic acid, 15% liquid paraffin, 1% polysorbate 20, 0.5% phenonip, 0.1% buffering agent, 0.075% sorbic acid and water to 100%.

EXAMPLE 6

Paint Composition

Paints in accordance with the invention can be prepared using the following materials in the proportions set out below:

| | | % w/v |
|---|---|---|
| cis-UCA | | 0.1–10 |
| Purified Water | | 0–60 |
| Dimethyl Sulphoxide | To | 100 |

The preferred composition for such a paint is 5% cis-UCA, 20% purified water and 75% dimethyl sulphoxide.

We claim:

1. A pharmaceutical composition comprising
   a topical preparation of a compound of general formula I, or a pharmaceutically acceptable salt thereof:

$$Q—R—X \qquad (I)$$

wherein Q is a substituted or unsubstituted pyrrolyl group, R is $CR^1{}_2—CR^2{}_2$, (cis)$CR^1{=}CR^2$, or (trans) $—CR^1{=}CR^2$, X is COOR³ or NR¹R⁴, and R¹–R⁴ are each independently, H, or an alkyl or an aryl group, in an amount for therapeutic treatment of a skin condition which is responsive to UV irradiation and is selected from the group consisting of polymorphic light eruption, actinic purrigo, solar urticaria acne vulgaris, alopecia areata, dermatitis herpetiformis, eosinophilic pustular folliculitis, erythrokeratoderma, chronic lichenoid GVH disease, granuloma annulare, histiocvtosis X, ichthyosis linearis circumflexa, lichen planus, pityriasis lichenoides, pityriasis rosea, pityriasis rubra pilaris, subcorneal pustular dermatoses, transient acantholytic dermatoses, psoriasis and atopic eczema.

2. The pharmaceutical composition of claim 1, wherein Q is unsubstituted, or substituted with F, Cl, Br, or $CH_3$.

3. The pharmaceutical composition of claim 1, wherein $R^1$–$R^4$ each, independently, are H, a lower alkyl group or a phenyl group.

4. The pharmaceutical composition of claim 1, wherein R is (cis)$CR^1$=$CR^2$.

5. The pharmaceutical composition of claim 1, wherein Q is unsubstituted.

6. The pharmaceutical composition of claims 1, 4 or 5, wherein $R^1$–$R^4$ are each H.

7. The pharmaceutical composition as claimed in claims 1, 2, 3, 4, 5 or 6, in admixture with a pharmaceutically acceptable excipient or carrier suitable for topical use.

8. The pharmaceutical composition of claim 7 comprising an ointment, gel, aerosol, wipe, cream, lotion or emulsion.

9. A method for treating a skin condition which is responsive to UV irradiation and is selected from the group consisting of polymorphic light eruption, actinic purrigo, solar urticaria, acne vulgaris, alopecia areata, dermatitis herpetiformis, eosinophilic pustular folliculitis, erythrokeratoderma, chronic lichenoid GVH disease, granuloma annulare, histiocytosis X, ichthyosis linearis circumflexa, lichen planus, pityriasis lichenoides, pityriasis rosea, pityriasis rubra pilaris, subcorneal pustular dermatoses, transient acantholytic dermatoses, psoriasis and atopic eczema, comprising:

topically applying to a subject in need of such treatment a therapeutic amount of the compound of claim 1, 2, 3, 4, 5 or 6.

10. The method of claim 9 wherein the compound is in an admixture with a pharmaceutically acceptable excipient or carrier.

11. The method of claim 10 wherein the compound is in an ointment, gel, aerosol, wipe, cream, lotion or emulsion.

12. A pharmaceutical composition comprising a topical preparation of a compound of general formula I, or a pharmaceutically acceptable salt thereof:

wherein Q is an unsubstituted pyrrolyl group, R is (cis) $CR^1$=$CR^2$, and $R^1$ and $R^2$ are both H, in an amount for therapeutic treatment of a skin condition which is responsive to UV radiation and is selected from the group consisting of polymorphic light eruption, actinic prurigo, solar urticaria, acne vulgaris, alopecia areata, dermatis herpetiformis, eosinophilic pustular folliculitis, erythrokertoderma, chronic lichenoid GVH disease, granuloma annulare, histiocytosis X, ichthyosis linearis circumflexa, lichen planus, pityriasis lichenoides, pityriasis rosea, pityriasis rubra pilaris, subcomeal pustular dermatoses, transient acantholytic dermatoses, psoriasis and atopic eczema.

13. The pharmaceutical composition of claim 12 which includes a pharmaceutically acceptable excipient or carrier suitable for topical use.

14. The pharmaceutical composition of claim 13 wherein the compound of general formula I is present in an amount of from about 0.1% w/w to about 10% w/w.

* * * * *

UNITED STATES PATENT AND TRADEMARK OFFICE
CERTIFICATE OF CORRECTION

PATENT NO. : 6,028,098
DATED : February 22, 2000
INVENTOR(S) : Goodman et al.

It is certified that error appears in the above-identified patent and that said Letters Patent is hereby corrected as shown below:

Claim 12 should read as follows:

12. A pharmaceutical composition comprising a topical preparation of a compound of general formula I, or a pharmaceutically acceptable salt thereof:

$$Q\text{-}R\text{-}X \quad (I)$$

wherein Q is an unsubstituted pyrrolyl group, R is $(cis)CR^1=CR^2$, and $R^1$ and $R^2$ are both H, X is $COOR^3$ or $NR^1R^4$, and $R^3$ and $R^4$ are both H, in an amount for therapeutic treatment of a skin condition which is responsive to UV radiation and is selected from the group consisting of polymorphic light eruption, actinic purrigo, solar urticaria, acne vulgaris, alopecia areata, dermatis herpetiformis, eosinophilic pustular folliculitis, erythrokertoderma, chronic lichenoid GVH disease, granuloma annular, histiocytosis X, ichthyosis linearis circumflexa, lichen planus, pityriasis lichenoides, pityriasis rosea, pityriasis rubra pilaris, subcorneal pustular dermatoses, transient acantholytic dermatoses, psoriasis and atopic eczema.

Signed and Sealed this

Eleventh Day of December, 2001

Attest:

NICHOLAS P. GODICI
Attesting Officer  Acting Director of the United States Patent and Trademark Office